United States Patent [19]

Marsella et al.

[11] Patent Number: 5,026,929

[45] Date of Patent: Jun. 25, 1991

[54] SYNTHESIS OF HIGHLY FLUORINATED AROMATIC COMPOUNDS

[75] Inventors: John A. Marsella; Guido P. Pez, both of Allentown; Anne M. Coughlin, Bethlehem, all of Pa.

[73] Assignee: Air Products and Chemicals, Inc., Allentown, Pa.

[21] Appl. No.: 477,289

[22] Filed: Feb. 8, 1990

[51] Int. Cl.$^5$ .................. C07C 17/24; C07C 17/00; C07C 25/13; C07C 25/18

[52] U.S. Cl. ................................. 570/146; 568/775

[58] Field of Search .............................. 570/146

[56] References Cited

U.S. PATENT DOCUMENTS 3,000,976  9/1961  Patrick et al. ................. 570/146
4,820,884  4/1989  Weigert ......................... 570/156

FOREIGN PATENT DOCUMENTS 19540  1/1987  Japan ........................... 570/146

OTHER PUBLICATIONS

B. Gething et al., "A New General Route to Aromatic Fluorocarbons", Nature, (London), vol. 183, pp. 588–589 (1959).
J. Barley et al., "Fluorinations with Complex Metal Fluorides", Journal of Fluorine Chemistry, 37, pp. 1–14 (1987).
P. Johncock et al., "The Semi-Micro Determination of Fluorine and Chlorine in Organic Compounds", Analyst, 84, pp. 245–247 (1959).
D. D. MacNicol et al., "New and Unexpected Reactivity of Saturated Fluorocarbons", Nature (London), vol. 332, pp. 59–61 (1988).

Primary Examiner—J. E. Evans
Attorney, Agent, or Firm—Mark L. Rodgers; William F. Marsh; James C. Simmons

[57] ABSTRACT

A process is disclosed for making a highly fluorinated aromatic compound by contacting a perfluorocycloalkane, such as perfluorodecahydronaphthalene, with a complex of a metal from Groups IA and IIA of the Periodic Table and an organic electron acceptor. The reaction is carried out in an organic solvent and under reducing conditions which are relatively moderate. Best results are obtained using a perfluorocycloalkane having 2–4 condensed rings and a complex of either sodium or lithium and benzophenone thereby making a perfluorinated condensed ring aromatic compound such as perfluoronaphthalene or perfluorophenanthrene.

10 Claims, No Drawings

SYNTHESIS OF HIGHLY FLUORINATED AROMATIC COMPOUNDS

FIELD OF INVENTION

This invention relates to a process for making highly fluorinated aromatic compounds by reduction of perfluorocycloalkanes.

BACKGROUND OF INVENTION

Highly fluorinated aromatic compounds such as perfluorophenanthrene have a number of potential uses, including uses as precursors to fluorinated chemical intermediates for making fluorosurfactants and biologically active compounds, but the commercialization of such uses has been limited by the difficulty in synthesizing them. While it is relatively easy to synthesize perfluorocycloalkanes, it is much more difficult to make a highly fluorinated aromatic compound.

Perfluorinated aromatic compounds have been made by the complete exchange of perchloroaromatic compounds with a suitable source of fluoride ions such as KF or HF. This method is not efficient because it requires the synthesis of the chlorinated intermediate and in addition requires either a catalyst or anhydrous conditions. Potassium fluorie is very difficult to dry and while anhydrous hydrogen fluoride can be obtained, this reactant usually requires a catalyst.

It has been known for many years that perfluoro- or highly fluorinated cycloaliphatic compounds can be converted to fluorinated aromatic compounds by high temperature defluorination or dehydrofluorination. Gething, et al. "A New General Route to Aromatic Fluorocarbons", *Nature* (London) 183, pages 588-9 (1959) discloses that perfluoronaphthalene can be made from perfluorodecohydronaphthalene by defluorination at 400°-600° C. over iron gauze. Bailey, et al., "Fluorinations With Complex Metal Fluorides", *J. of Fluorine Chemistry*, 37, pages 1-14 (1987) reported defluorination of saturated cyclic fluorocarbons over fully spent cesium trifluorocobaltate at 400° C. Attempts by others to effect reactions of perfluorinated aliphatic compounds have given complete defluorination to non-fluorine-containing products.

Johncock, et al. "The Semi-Micro Determination of Fluorine and Chlorine in Organic Compounds", *Analyst*, 84, pages 245-7 (1959) discloses that fluoro- and chlorofluoro compounds can be totally decomposed for analytical purposes by reaction with a biphenyl-sodium-dimethoxyethane complex. This author states that other aromatic compounds such as benzophenone and other ethers such as tetrahydrofuran have been tried but were rejected.

MacNicol and Robertson, *Nature* (London), 332, pages 59-61 (1988) states that saturated fluorocarbons are noted for outstanding chemical inertness, requiring extreme conditions such as treatment with metals at 500° C. to react. These authors report, however, reacting perfluorodecahydronaphthalene with arenethiolate nucleophiles in a dipolar aprotic solvent to form organic products containing no fluorine and including octakis(phenylthio)naphthalene under ambient conditions as well as at temperatures in the range of 60°-70° C. It should be noted that no fluorinated aromatics or other fluorine containing organic products were reported.

U.S. Pat. No. 4,820,884 discloses a defluorination process for preparing unsaturated aliphatic or cycloaliphatic perfluorocarbons by contacting the corresponding perfluoroalkane with activated carbon at a temperature of from about 300° to 500° C.

SUMMARY OF THE INVENTION

We have discovered a process for making a highly fluorinated aromatic compound by contacting, under reducing conditions, a perfluorocycloalkane with a complex of a metal of either Group IA or IIA of the Periodic Table and an organic electron acceptor in a suitable organic solvent. The reaction occurs at low to moderate temperatures to give highly fluorinated aromatic compounds.

DETAILED DESCRIPTION OF THE INVENTION

The perfluorocycloalkanes which are used as the starting materials for the practice of this invention are relatively easy to obtain. They can be synthesized by known fluorination procedures, but many are commercially available. These perfluorinated compounds have 1-4 rings in their chemical structure, but it is preferred to practice the invention with perfluorocycloalkanes having 2-4 condensed rings. Examples of suitable perfluorinated substrates include perfluorocyclohexane, perfluorodecahydronaphthalene, perfluoroperhydrophenanthrene, and other perfluoroperhydro-derivatives of anthracene, naphthacene, triphenylene, pyrene, chrysene, perylene, benthantacene and the like. Additionally, as used herein, perfluorocycloalkane only includes saturated cyclic fluoroalkanes which do not contain any perfluorinated alkyl groups substituted on the ring.

The controlled defluorination reactions are carried out at low to moderate temperature, for example temperatures ranging from $-78°$ C. to $75°$ C. In a suitable organic solvent using alkali or alkaline earth metal/organic radical anion complexes formed between reducing metals and organic electron acceptors. Such metal complexes are well known to those skilled in the art and can be made from reducing metals such as the metals of Group IA or IIA of the Periodic Table, such as lithium, sodium, rubidium, cesium, magnesium, calcium and the like. Preferably the reducing metal is either lithium or sodium.

The organic electron acceptor moderates the reduction of the metal so that products are formed that can be readily isolated. The preferred electron acceptor is benzophenone but other compounds can be used under suitable conditions, such as napthacene, benzil, naphthalene, anthracene and the like.

The reaction is carried out in a solution of an organic solvent and any such solvent can be used which does not interfere with the defluorination process. A preferred and highly convenient solvent for this purpose is tetrahydrofuran.

The invention is further described by the following examples which are meant to be illustrative only and should not be construed to limit our our invention unduly.

In the examples the organic solvent, tetrahydrofuran, was refluxed overnight over calcium hydride and distilled under nitrogen. It was then further dried and deoxygenated by treatment with the disodium complex of the benzophenone dianion. Aliquots for use in reactions were then vacuum distilled from the storage vessel containing this violet solution. (Solutions containing the radical anion are blue. While the radical anion is an effective oxygen scavenger, it is less effective than the dianion in in removing water.) Sodium metal was purchased in paraffin oil from Aldrich and rinsed in hexane prior to use; benzophenone (Aldrich, gold label) was used as received.

Perfluorodecahydronaphthalene and perfluoroperhydrophenanthrene were prepared by the reaction of their hydrocarbon analogues over cobalt trifluoride. Perfluorodecahydronaphthalene was determined to have a free fluoride ion content of <0.1 ppm by analysis of a water wash, and a residual hydrogen level of 3 ppm, by FT-IR analysis. Analysis of perfluoroperhydrophenanthrene by these methods showed free fluoride to be 0.2 ppm and residual hydrogen to be 11 ppm. It was also found to contain about 16% perfluoro (2, n-butyldecahydronaphthalene) as determined by gas chromatographic analysis. Perfluoromethylcyclohexane (97%) and perfluorocyclohexane (99%) were purchased from Aldrich; perfluorooctane (99%) was obtained from PCR. The fluorocarbons were dried over activated molecular sieves (4A) overnight, thoroughly degassed by at least four freeze/thaw cycles and vacuum distilled. They were then stored in a glove box ($N_2$ atmosphere).

The following chemicals were obtained from commercial sources for use as comparison standards: Octafluoronaphthalene (Alfa), octafluorotoluene (Alfa), hexafluorobenzene (Aldrich), pentafluorobenzene (Aldrich) and 2,3,5,6-tetrafluorophenol. The latter was also prepared by a literature method.

Gas chromatography was performed on a model 5880 Hewlett Packard gas chromatograph using a flame ionization detector and a capillary column. An SPB-5 bonded phase column was used (Supelco, 0.24 mm × 30 m, 1.0 μm film thickness). The column was held at 50° C. for four minutes and then ramped by 6° C./min. to a final temperature of 220° C. Using these conditions, tetrahydrofuran eluted at approximately 3.8 min. and benzophenone at 32.8 min.

GC-MS determinations were carried out on Finnegan models 1020, 4500 and ITD GC-MS instruments. Fluorine-19 NMR spectra were recorded at room temperature using an IBM SY-200 FT-NMR spectrometer operating at 188.3 MHz, equipped with a 5 mm $'H/^{19}F$ pretuned probe. Chemical shifts are referenced to $CFCl_3$ with resonances upfield from this standard being assigned negative values.

To characterize the products, the reaction vessel was opened to air and the sample of the reaction mixture was analyzed by gas chromatography. All volatiles were then stripped in vacuo and analyzed by gas chromatography and $^{19}F$ NMR. The involatile solids were then extracted with $D_2O$ for purpose of analyzing for $F^-$ and the remaining residue, wet with $D_2O$ was then dissolved in $d_6$-acetone. The procedure allowed for analysis of all reaction products by NMR spectroscopy. Also, the actual reaction mixture as well as the volatile liquid products were examined by gas chromatography.

EXAMPLE 1

A 15 ml glass vessel equipped with a vacuum teflon stopcock and a magnetic stirring bar was placed in an $N_2$ filled glove box and charged with 0.05 g Na (2.2 mmol) and 0.52 g benzophenone (2.9 mmol). The vessel was sealed, brought out of the glove box and attached to a vacuum line. After evacuation, the vessel was cooled in liquid nitrogen and ca. 10 ml of THF was vacuum distilled into it from the violet solution described above. Upon thawing and stirring, the blue color due to the radical anion formed. Stirring was continued for ca. 2 h to assure that all of the sodium had reacted. The blue solution was then placed in a cold bath maintained at ~ −70° C. Under a nitrogen purge, 90 μl perfluorodecahydronaphthalene (0.174 g, 0.37 mmol) was added to the flask via syringe through a septum sealed port. The flask was degassed and allowed to warm to room temperature while stirring over a period of 1½ hours. During this time the color changed from deep blue to dark red-brown. Gas chromatographic analysis of the final reaction solution yielded a new peak which eluted at about 19.3 min. GC-MS analysis identified the product as octafluoronapthalene.

The volatile components were stripped in vacuo. The fluorine-19 NMR spectrum of the $D_2O$ extract of the remaining involatile solids yielded a single resonance at −122.5 ppm, which corresponds to the fluoride ion. The fluorine-19 NMR spectrum of the $d_6$-acetone extract of the involatile solids showed resonances at −146.3 and −155.1 ppm. This spectrum matched that of a commercial sample of octafluoronapthalene and is consistent with the literature data.

Products from 11 reactions according to the above procedure were analyzed by gas chromatography. In the first 10 reactions, 0.37 mmol perfluorodecalin and 2.2 mmol of sodium were used. An excess of benzophenone was used for each reaction. Fairly consistent yields based on the sodium of 68–86% were observed for these reactions. Although the amount of sodium was increased to the stoichiometric amount for the 11th reaction, a somewhat lower yield of 61% was observed.

The above reaction was also carried out using lithium instead of sodium and produced an octafluoronaphthalene yield of 36%.

This example demonstrates the conversion of perfluorodecahydronaphthale to perfluoronaphthalene under very mild temperature conditions.

EXAMPLE II

A 100 ml glass vessel was charged with 0.5 g Na (0.021 mole) and 5.2 g benzophenone (0.029 mole) in a nitrogen filled glove box as described in Example I. Approximately 100 ml THF was vacuum distilled into the vessel to form the blue radical anion solution. After stirring for two hours, the flask was placed in a cold bath (−70° C.) and 900 μl perfluorodecahydronaphthalene (1.736 g, 0.0037 mole) was added to the flask as in Example I. The flask was allowed to warm to room temperature over a period of 1½ hours, during which time the color changed to dark red-brown.

The flask was opened in the air and the THF was removed by bubbling nitrogen through the solution, leaving a brick-red solid.

A glass column (24" height × 1" diameter) equipped with a teflon stopcock at the bottom and a solvent bulb and gas inlet valve at the top was packed with 40 g silica gel (Aldrich, BET surface 500m²/g, pore volume 0.75 cm³/g, 230–400 mesh, 60A) using 5 psig nitrogen pressure and 1000 ml 100% hexane. The column was purged dry with nitrogen before use.

The brick-red solid from above was dissolved in about 10 ml hexane. This solution was transferred by pipette to the top of the column. The solvent bulb was filled with 1000 ml hexane and about 5 psig nitrogen pressure was applied to the column. Forty 20 ml fractions were collected. The octafluoronapthalene was found in fractions 10 through 28. The solvent was removed by rotovap leaving 0.369 g (65% isolated yield)

of a fluffy white crystalline solid with melting point 83°-84° C. (literature: 87°-88° C.). Gas chromatographic analysis of the solid dissolved in a few mls of THF showed three peaks. The major peak was octafluoronapthalene, eluting at 19.3 minutes. The other two peaks, with retention times 19.1 and 20.2 minutes were identified by GC-MS to be di- and mono-hydro-perfluoronapthalenes, respectively. The sample contained 94% octafluoronapthalene and 6% of the hydrogen containing perfluoronapthalenes, as determined by area percent on the gas chromatograph.

EXAMPLE III

This reaction was run as described in Example I using a 100 ml flask, 0.7032 g Na (0.0306 mole), 8.2 g benzophenone (0.045 mole), 1.16 ml perfluoroperhydrophenanthrene (2.34 g, 0.0037 mole) and 100 ml THF.

The involatile solids from this reaction and several other smaller scale reactions were combined and dissolved in about 10 ml hexane. Decafluorophenanthrene was separated from this solution using column chromatography as described in Example II. Forty 20 ml fractions were collected. The decafluorophenanthrene was found in fractions three, four and five. The solvent was removed by rotovap leaving 0.24 g of pale yellow crystalline solid. Gas chromatography analysis of the solid dissolved in a few mls of THF showed four peaks. The major peak was decafluorophenanthrene, eluting at 32.1 minutes. The other three peaks, with retention times 32.3, 32.8 and 32.9 minutes were identified by GC-MS to be mono-, di-, and tri-hydro-per-fluorophenanthrenes. The sample was run through the chromatography column two times more in an attempt to separate the decafluorophenanthrene from these hydrogen containing species. The final sample contained 82% decafluorophenanthrene, and 18% of the hydrogen containing perfluorophenanthrenes, as determined by area percent on the gas chromatograph.

The products from 3 reactions were analyzed by gas chromatography and for each of these reactions for which an excess of perfluoroperhydrophenanthrene (0.39 mmol) and 3.38 mmol sodium was used, yields of decafluorophenanthrene (based on sodium) ranged from 40–56%.

EXAMPLE IV

The reaction was run as described earlier using 0.0402 g Na, 0.532 g (moles) benzophenone, 0.0996 g perfluorocyclohexane and 10 ml THF. The perfluorocyclohexane was vacuum transferred to the radical anion solution. Since no color change was seen after the reaction flask had warmed to room temperature, the flask was heated at 52° C. for 3.5 hours, followed by stirring at room temperature for an additional twelve hours. Still no color change was observed.

Analysis of the reaction solution was carried out without exposing the solution to air. Samples were removed from the reaction flask inside the nitrogen glove box and placed in septum sealed vials. Gas chromatographic analysis of one of these samples did not show any new peaks.

GC-MS analysis was performed on three samples from the reaction solution. The first sample was analyzed directly without exposure to air. The only product observed was a trace of tetrafluorobenzene. The position of the fluorines in the tetrafluorobenzene could not be definitely determined. Air was bubbled through the second sample before analysis, but its total ion chromatogram (GC/MS) was virtually identical to that of the first sample. The third sample was analyzed after the addition of a few drops of water. No tetrafluorobenzene was seen, but a trace of tetrafluorophenol (position of fluorines uncertain) was observed. The third sample was re-analyzed twenty-two days after the addition of water, showing a significant increase in the size of the tetrafluorophenol peak.

EXAMPLE V

The procedure for Example IV was repeated, but the reaction solution was treated by removing the volatiles in vacuo and the residue was washed, in air, first with $D_2O$ and then with $d_6$-acetone. Fluorine-19 NMR and GC-MS both showed the presence of 2,3,5,6-tetrafluorophenol. This example shows that partially fluorinated as well as perfluorinated aromatic compounds can be made using the process of this invention.

Other aspects and embodiments of our invention will be apparent to those skilled in the art from the above description without departing from the spirit or scope of our invention.

EXAMPLE VI (COMPARATIVE)

Attempts were made to react perfluoro-2-isopropyl-decahydronaphthalene with sodium benzophenone. The reaction described in Example 1 above was run with 0.647 g benzophenone, 0.0508 g sodium, 100 ml perfluoro-2-isopropyldecahydronaphthalene and 10 ml tetrahydrofuran. The color turned from a deep blue to a dark brown as the solution warmed to room temperature. However, no new peaks were seen in the gas chromatography analysis of the solution. GC-MS analysis of the solution showed no organic reduction products. These results indicate that perfluorinated alkyl substituents on the ring may interfere with the selective reduction chemistry observed in their absence; i.e. Examples I-V.

We claim:

1. A process for making a highly fluorinated aromatic compound which comprises contacting a perfluorocycloalkane with a complex of a Group IA or IIA metal and an organic electron acceptor in an organic solvent under reducing conditions.

2. The process of claim 1 wherein said perfluorocycloalkane has 2 to 4 condensed rings.

3. The process of claim 1 wherein said metal is lithium or sodium.

4. The process of claim 1 wherein said electron acceptor is benzophenone.

5. The process of claim 1 wherein said organic solvent is tetrahydrofuran.

6. The process of claim 1 wherein said reducing conditions include a temperature in the range of −78° to 75° C.

7. The process of claim 1 wherein said compound is a perfluorinated condensed ring aromatic.

8. A process for making a perfluorinated condensed ring aromatic compound which comprises reducing a perfluorocycloalkane having 2 to 4 condensed rings by reaction with a sodium or lithium complex with benzophenone in an organic solvent at a temperature in the range of −78° to 75° C.

9. The process of claim 8 wherein said compound is perfluoronaphthalene and said perfluorocycloalkane is perfluorodecohydronaphthalene.

10. The process of claim 8 wherein said compound is perfluorophenanthrene and said perfluorocycloalkane is perfluorohydrophenanthrene.

* * * * *